United States Patent [19]
Walker

[11] Patent Number: 6,110,866
[45] Date of Patent: Aug. 29, 2000

[54] SURFACTANT COATED PRODUCTS AND METHODS FOR THEIR USE IN PROMOTING PLANT GROWTH

[75] Inventor: Richard T. Walker, Senatobia, Miss.

[73] Assignee: Jay-Mar, Inc., Plover, Wis.

[21] Appl. No.: 09/385,987

[22] Filed: Aug. 30, 1999

Related U.S. Application Data

[60] Provisional application No. 60/111,462, Dec. 9, 1998, and provisional application No. 60/115,088, Jan. 7, 1999.

[51] Int. Cl.[7] ............................. A01N 3/02; A01N 59/00; A01N 59/14
[52] U.S. Cl. ............................................ 504/118; 119/122
[58] Field of Search .................... 504/118, 122, 504/119

[56] References Cited

U.S. PATENT DOCUMENTS

| | | | |
|---|---|---|---|
| 4,931,074 | 6/1990 | Marguier | 148/248 |
| 5,026,734 | 6/1991 | Browning | 514/723 |
| 5,141,963 | 8/1992 | Browning | 514/723 |
| 5,143,939 | 9/1992 | Browning | 514/723 |
| 5,391,542 | 2/1995 | Browning | 504/351 |
| 5,429,654 | 7/1995 | Swarup | 71/64.07 |
| 5,484,600 | 1/1996 | Sjogren | 424/405 |
| 5,516,520 | 5/1996 | Yang et al. | 424/408 |
| 5,532,305 | 7/1996 | Matsuzaki et al. | 525/54.2 |
| 5,565,407 | 10/1996 | Southard | 504/116 |
| 5,576,008 | 11/1996 | Yang et al. | 424/408 |
| 5,652,196 | 7/1997 | Luthra et al. | 504/116 |
| 5,750,130 | 5/1998 | Ferrell et al. | 424/417 |

FOREIGN PATENT DOCUMENTS 62-198641  9/1987  Japan.

*Primary Examiner*—Jose' G. Dees
*Assistant Examiner*—Alton Pryor
*Attorney, Agent, or Firm*—Howrey Simon Arnold & White, LLP

[57] ABSTRACT

Mixed agricultural compositions, and methods for their use are disclosed. The agricultural compositions are prepared by a process comprising mixing together nonionic polyglycol ethers, or oxidation products thereof, and a carrier material. The carrier typically comprises an aqueous or non-aqueous liquid solvent or a solid core material, such as a fertilizer. The carrier may further comprise biologically active agents such as herbicides, insecticides, chemosterilants, nematicides, and fungicides. The agricultural compositions can be used to promote the growth of plants in soil, to improve the control of agricultural pests, and to enhance soil bioremediation.

29 Claims, No Drawings

SURFACTANT COATED PRODUCTS AND METHODS FOR THEIR USE IN PROMOTING PLANT GROWTH

This application claims priority from U.S. provisional applications 60/111,462 filed Dec. 9, 1998 and 60/115,088 filed Jan. 7, 1999.

FIELD OF THE INVENTION

The present invention relates to mixed agricultural compositions and methods for their use. Specifically, a solid core material comprising a fertilizer, pesticide or anti-caking agent is mixed with a nonionic polyglycol ether surfactant or the oxidized products thereof. The mixed agricultural compositions may be used to improve plant growth, enhance pest control, and facilitate bioremediation. When applied in the field, the mixed agricultural compositions maintain their efficacy for longer periods of time relative to non-mixed fertilizers, pesticides or surfactants alone.

BACKGROUND OF THE INVENTION

It is known that gradual release of fertilizer nutrients and biologically active agents such as pesticides into the soil is more advantageous for pest control, plant growth, and seed germination, as this avoids undesirable plant toxicity resulting from sudden increases in soil concentrations of applied substances.

Many controlled release methods for fertilizers and pesticides have previously been disclosed. For example, in U.S. Pat. No. 5,484,600, Sjogren discloses a method for making a composite particle capable of releasing insecticides at a slow or controlled rate. In U.S. Pat. No. 5,576,008, Yang et al. disclose a method for the microencapsulization of insecticides into a urea-formaldehyde resin. In U.S. Pat. No. 5,516,520, Yang et al. disclose a method of preparation and use of a pesticide encapsulated in a starch-borax-urea matrix for controlled release. In U.S. Pat. No. 5,565,407, Southard discloses improved bioactive agent release-extending compositions of native, undenatured starch and biodegradable synthetic polymers. In U.S. Pat. No. 5,652,196, Luthra et al. disclose products for the variable controlled release of water soluble plant nutrients consisting of a core of water soluble agent coated with an organic film-forming thermoplastic or thermosetting compound and a thermoplastic resin to control release. In U.S. Pat. No. 5,429,654, Swarup discloses a method of improved fertilizer release control comprising coating a fertilizer with a neutralized, sulfonated EPDM polymer having a measurable degree of crystallinity. In U.S. Pat. No. 5,750,130, Ferrell et al. disclose a method of applying a pesticide to inert organic or inorganic granular substrates using a carrier compound to improve adhesion of the pesticide to the substrate and to improve control over the release of the pesticide.

It is desirable to avoid the use of foreign materials or materials which are not otherwise useful for growing plants when developing methods for the more effective utilization of fertilizers and pesticides, as this allows for enhanced growth and protection of plants without the introduction of complex and expensive matrix components.

In U.S. Pat. Nos. 5,391,542 and 5,143,939, Browning discloses the use of surfactants such as the TERGITOL series of surfactants (TERGITOL is a registered trademark of Union Carbide Corporation, Danbury, Conn.) as a liquid soil additive to enhance the germination and subsequent growth of plants. Browning also describes the use of the liquid soil additive as a method of nematode, worm, mite, and fungus control. However, the surfactant is only effective for a limited period of time following application to the soil.

There exists a need in the art for an improved soil treatment which is efficacious over a longer period of time and avoids the use of extra foreign materials or matrix components. Such a treatment should ideally enhance plant germination and growth while allowing for the control of agricultural pests. The treatment should also control the release of the agricultural products so as to prevent concentration fluctuations that may be toxic to plants. In so doing, the number of required applications will be reduced due to a decrease in the amount of leaching.

SUMMARY OF THE INVENTION

The present invention is directed to an agricultural composition prepared by a process comprising mixing together a nonionic polyglycol ether surfactant, or the oxidized products thereof, with a carrier material. The carrier material typically comprises an aqueous or non-aqueous liquid solvent or a solid core material, such as an organic fertilizer, inorganic fertilizer, pesticide, or anti-caking agent. The solid core material is preferably provided as a powder, granule, pellet, or any other compatible solid form. The carrier material may generally be any formulation having agricultural utility which is compatible with the present invention.

As used herein the term "mixing" includes the activities of mixing, contacting, blending, coating, applying, impregnating, commingling, amalgamating, and coalescing.

The carrier material may further comprise a biologically active agent. The biologically active agent is typically selected to bestow additional functional properties to the mixed agricultural composition. Exemplary biological agents include herbicides, insecticides, chemosterilants, nematicides, and fungicides.

The carrier material is typically mixed with a nonionic polyglycol ether, more preferably an alcohol ethoxylate, fatty alcohol ethoxylate, or alkylphenol ethoxylate, and most preferably an alkyoxypolyethyleneoxy-ethanol or nonyl phenol ethoxylate. Even more preferred is mixing the oxidation products of the nonionic polyglycol ether surfactants with carrier material. The nonionic polyglycol ether surfactant or oxidation products thereof are generally used at a concentration of about 400 grams to about 7700 grams per U.S. ton of solid core material. The mixed agricultural composition preferably is applied in a field at a rate between about 125 pounds and about 1000 pounds per acre.

These mixed agricultural compositions can be useful for promoting the growth of plants, for controlling various agricultural pests, and for soil bioremediation. These agricultural compositions maintain their efficacy for longer periods of time relative to non-mixed fertilizers, pesticides or surfactants alone. In addition, they also exhibit diminished toxic effects when compared with those normally associated with the application of pesticides and surfactants provided as unmixed formulations.

DETAILED DESCRIPTION OF THE INVENTION

The present invention relates to an agricultural composition prepared by a process comprising mixing a nonionic polyglycol ether surfactant, or the oxidized products thereof, and a carrier material, methods for producing the composition, and uses thereof. In particular, the polyglycol ether or oxidation products thereof are mixed with an aqueous or non-aqueous liquid solvent or a solid core material. The solid core material may comprise a soil additive such as an organic fertilizer, inorganic fertilizer, anti-caking agent, herbicide, insecticide, chemosterilant, nematicide, fungicide or combinations of such materials.

The solid core material generally comprises a powdered, particulate, granular, pelleted, or any other compatible solid form of an organic or inorganic fertilizer. The organic fertilizer may be any compatible organic fertilizer and is preferably HOUACTINITE (Houston, Tex.), or MILORGANITE (Milwaukee, Wis.). The inorganic fertilizer may generally be any fertilizer having agricultural utility including ammonium nitrate, ammonium sulfate, ammonium polyphosphate, calcium sulfate, calcium nitrate, calcium sulfate, diammonium phosphate, triple super phosphate, single super phosphate, lime or limestone, magnesium sulfate, manganese sulfate, monoammonium phosphate, monocalcium phosphate, potassium nitrate, potassium chloride, potassium magnesium sulfate, sulfate of potash, sodium nitrate, sulfur-coated urea, borax, pelleted fertilizers, fertilizers coated for slow release, or mixtures thereof.

The solid core material may also include various inert substances which may not directly contribute to the overall nutrient value of the agricultural composition. Such substances may include solid carriers, drying agents, or anti-caking agents such as diatomaceous earth, calcium sulfate, corn cob particulate, bentonite clay, vermiculite, or combinations of these substances.

The solid core material may further comprise a biologically active agent. The biologically active agent is typically selected to bestow additional functional properties to the mixed agricultural composition. Exemplary biological agents include herbicides, insecticides, chemosterilants, nematicides, and fungicides.

The herbicide may generally be any herbicidal agent compatible with the present invention. The herbicide preferably is an amide, aromatic acid, arsenical, benzoylcyclohexanedione, benzofuranyl alkylsulfonate, carbamate, carbanilate, cyclohexene oxime, cyclopropylisoxazole, dinitroaniline, dinitrophenol, diphenyl ether, halogenated aliphatic, imidazolinone, inorganic, nitrile, organophosphorus, phenoxy, phenylenediamine, pyrazolyloxyacetophenone, pyrazolylphenyl, pyridazinone, pyridine, pyrimidine diamine, quaternary ammonium, thiocarbamate, thiocarbonate, triazine, triazole, triazolopyrimidine, uracil, urea, unclassified herbicide, or a mixture thereof, more preferably is a dinitroaniline herbicide, and most preferably is trifluralin.

The insecticide may generally be any insecticidal agent compatible with the present invention. The insecticide preferably is antibiotic, arsenical, botanical, carbamate, dinitrophenol, fluorine, formamidine, fumigant, hydrazide, growth regulatory, nereistoxin analogue, nitromethylene, organochlorine, organophosphorus, oxadiazine, pyrazole, pyrethroid, pyridine, unclassified insecticide, or a mixture thereof.

The chemosterilant may generally be any chemosterilant agent compatible with the present invention. The chemosterilant is preferably apholate, bisazir, busulfan, diflubenzuron, dimatif, hemel, hempa, metepa, methiotepa, methyl apholate, morzid, penfluron, tepa, thiohempa, thiotepa, tretamine, or a mixture thereof.

The nematicide may generally be any nematicidal agent compatible with the present invention. The nematicide is preferably an antibiotic, carbamate, organophosphorus, unclassified nematicide, or a mixture thereof.

The fungicide may generally be any fungicidal agent compatible with the present invention. The fungicide is preferably an aliphatic, anilide, antibiotic, aromatic, benzimidazole, benzimidazole precursor, carbamate, conazole, copper, dicarboximide, dinitrophenol, dithiocarbamate, imidazole, mercury, morpholine, organophosphorus, organotin, oxazole, phenylsulfamide, phenylurea, pyridine, pyrimidine, quinoline, quinone, quinoxaline, thiazole, thiocarbamate, triazole, xylylalanine, unclassified fungicide, or a mixture thereof.

The carrier material is typically mixed with a nonionic polyglycol ether surfactant, preferably an alcohol ethoxylate, fatty alcohol ethoxylate, or alkylphenol ethoxylate, more preferably an alkyoxypolyethyleneoxyethanol represented by the formula:

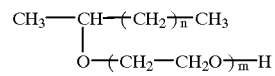

wherein m and n are integers, n is from about 9 to about 15, and m is from about 3 to about 40, more preferably n is from about 9 to about 11 and m is about 15; or a nonyl phenol ethoxylate represented by the formula:

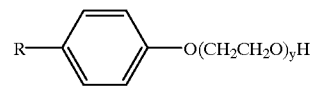

wherein R is a straight or branched carbon chain containing from about 1 to about 30 carbon atoms and y is an integer between about 5 and about 15, more preferably R is about 9 carbon atoms and y is about 9 to about 10; and most preferably an oxidation product of the polyglycol ether surfactant.

Alternatively, the carrier material may be mixed with an oxidized product of any of the above surfactants.

Exemplary surfactants include those of the TERGITOL 15-S and the NP series, or oxidized products thereof Th e surfactant is preferably TERGITOL 15-S-9 or NP-9 (Union Carbide, Danbury, Conn.).

The applicants have found the use agricultural compositions with oxidized products of the surfactants to provide unexpectedly increased plant growth promoting and surprisingly enhanced bioremediative activities when compared with compositions containing virgin surfactants. Therefore the oxidized products of the surfactant may be preferably used. The surfactant may b e easily oxidized by commonly used oxidizing agents. Oxidation is defined as a loss of electrons or a raising of the oxidation state. Any suitable oxidizing agents may be used; these include but are not limited to naphthaleneacetic acid, chromic acid, potassium permanganate, or sodium hypochlorite (bleach).

The oxidation reaction may preferably oxidize one or more of the susceptible bonds within the surfactant, including but not limited to, any of the C—C, C—O, O—H, or C—H bonds in the surfactant. This oxidation may result in the cleavage of one or more of the surfactant's covalent bonds resulting in the liberation of one or more breakdown products. Alternatively, the oxidation may occur without internal bond cleavage. The oxidation preferably converts the surfactant's primary alcohol functional group to an aldehyde moiety.

Suitable reaction conditions for the oxidation of polyglycol ethers are well known to those of ordinary skill in the art (*Organic Chemistry*, Stanley H. Pine, McGraw-Hill Book Company, New York, 1987). The quantity of oxidizing agent used, the length of time required for oxidation to occur, and other reaction conditions for the oxidation of the polyglycol ether will vary depending on the oxidizing agent used. For example five gallons of polyglycol ether surfactant mixed with two to ten gallons of bleach and stirred for one to five hours.

The surfactant preferably is applied to the solid core material at a concentration between about 400 grams and about 7700 grams per U.S. ton of solid core material, and more preferably between about 400 grams and about 2900 grams per U.S. ton of solid core material.

The surfactant is typically provided in a liquid form. For instance, a liquid surfactant containing greater than about 97% (v/v) alkyoxypolyethyleneoxyethanol is commercially available as TERGITOL 15-S-9 (Union Carbide, Danbury, Conn.). This solution may be directly applied to the solid core material. Alternatively, the surfactant may be diluted with a solvent prior to application to the solid core material. More preferably the surfactant is oxidized and then applied. The liquid surfactant is preferably sprayed onto the solid core material.

The mixture of surfactant and solid core material may become wet and difficult to manage when the quantity of surfactant added reaches the upper range of the application amount. If the mixture becomes wet, drying agent components, such as bentonite clay or calcium sulfate, may be added in an amount sufficient to reduce the moisture level of the composition. The amount of drying agent added is typically between about 5 pounds and about 50 pounds per U.S. ton of solid core material.

Dry fertilizers are often blended using large mixing devices or payloaders in which the fertilizer and various additives have been added. Transfer of scoopfuls of components into the mixture with a spreading action eventually produces a homogeneous mixture. During the process of mixing, an appropriate quantity of surfactant (as described above) may be sprayed onto the mixture to produce a uniform coating of the surfactant on the fertilizer blend. In addition, an appropriate concentration of a biologically active agent, such as a pesticide or herbicide, may be added to the mixed fertilizer blend. The biologically active agent is mixed with the fertilizer so that the agent is evenly distributed in the final product. The use of a surfactant greatly aids the process of impregnation of biologically active agents into fertilizer granules, presumably due to the enhanced penetrating qualities often observed with surfactants. The mixed agricultural composition preferably is used in the field at a rate between about 125 and about 1000 pounds per acre.

The invention is further directed to methods of using the above mixed agricultural compositions to promote plant growth in soil and enhance control of various agricultural pests. The method of promoting the growth of plants in soil generally comprises the steps of obtaining an agricultural composition mixed with a nonionic surfactant (as described above), and applying the composition to the soil.

Use of the surfactant-coated fertilizer compositions may allow the plants to more effectively utilize the fertilizer nutrients by reducing surface tension at the plant-water interface. This enhances the ability of the nutrient solution to cover and penetrate plant surfaces. The surfactant and nutrients are released into the soil from the fertilizer granules in a gradual and sustained manner by natural erosion processes.

The mixed agricultural compositions can also be used for control of various agricultural pests. This method generally comprises the steps of obtaining an agricultural composition mixed with a nonionic surfactant (as described above), and applying the composition to the soil. The agricultural composition may further comprise a biological agent such as a herbicide, insecticide, chemosterilant, nematicide, or fungicide.

By incorporating these biological agents into a mixed agricultural composition, the release of these biological agents is controlled and maintained over an extended period of time. This sustained release is generally superior to immediate release because it increases the time over which the treatment is effective and reduces the deleterious effects on plants due to high concentrations of these agents being released immediately following application. For example, biologically active agents such as pesticides are often toxic to plants during the sudden concentration "spike" immediately following application. The mixed agricultural compositions maintain a continual steady rate of release, thus avoiding toxic "spikes" in concentration.

Additionally, leaching of these biologically active agents into groundwater is reduced due to the controlled release properties of the mixed agricultural composition. At any given time, only a fraction of the total applied quantity of biologically active agent will be free in the soil to be washed off the field by rainfall or irrigation. Consequently, fewer applications of the agricultural composition are required as the applied agent remains on the field longer. Since an increased percentage of the agricultural composition will remain in the soil for a longer period of time, the total quantity of biologically active agent needed for the initial application is reduced. This decreases the total cost and also benefits the environment.

Agricultural compositions comprising polyglycol ethers or oxidation products thereof can be used to facilitate the bioremediation of contaminated soil. Bioremediation involves the use of living organisms to break down organic and inorganic contaminants into more basic components, thereby removing environmental pollutants, restoring contaminated sites, and preventing the accumulation of further pollutants. Generally, bioremediation is accomplished using bacteria, although other microorganisms, namely fungi and algae, have been used. See, for example, Ronald M. Atlas, *Chemical & Engineering News,* Apr. 3, 1995, pp. 32–42. The present invention is believed to function in part by serving as a nutrient source for the microorganisms responsible for bioremediation.

There are a variety of chemicals which may be refractory to spontaneous chemical breakdown and thus persist in the environment. Such contaminants may or may not be inherently toxic to the environment; for instance nitrates are not inherently toxic (minimum quantities are essential in order for most plants to thrive), however, excessive quantities of nitrates may have deleterious ecological effects.

Potential targets for bioremediation for use with the present invention may include any common inorganic or organic contaminant found in the environment and more preferably includes pesticides, insecticides, growth regulators, growth inhibitors, toxicants, bactericides, attractants, repellents, hormones, molluscicides, defoliants, chemosterilants, fumigants, systemics, rodenticides, avicides, detergents, surfactants, nematicides, acaricides, miticides, predicides, herbicides, agricultural chemicals, algicides, fungicides, sterilants; polycyclic aromatic hydrocarbons (PAH's), polychlorinated biphenyls (PCB's), greasy wastes, solvents, crude oil, diesel fuel, waste oil, Bunker "C" oil, phenolics, halogenated hydrocarbons, citrus juice processing wastes, terpene alcohols, starchy carbohydrates, and the like.

Specific organic contaminants may include anthracene, chlorotoluenes, chrysene, cresols, di-N-octylphthalate, dichlorobenzene, dichlorethanes, dichloropropanes, dichlorotoluene, 2-ethoxyethanol, ethylene glycol, ethylene glycol monoethyl ether acetate, ethylbenzene, fluorene, isoprenoids, methyl ethyl ketone, methylene chloride, naphthalene, pentachlorophenol, phenanthrene, 1,1,2,2-tetrachloroethane, toluene, 1,1,2-trichloroethane, trichloroethylene, benzoate, chlorobenzoates, methanol, ethyl acetate, cyclohexanone, ethylbenzene, 2,4-dichlorophenoxyacetic acid, 2,4,5 -trichlorophenoxyacetic acid, m,o,p-xylene, butyl acetate, camphor, hexane, heptane, octane, nonane, d-limonene, linalool, geraniol, citronellol.

Herbicides are a particularly common contaminant in agriculture. Classes of herbicidal contaminants found in the soil may include: amides, aromatic acids, arsenicals, benzoylcyclohexanediones, benzofuranyl alkylsulfonates, carbamates, carbanilates, cyclohexene oximes, cyclopropylisoxazoles, dinitroanilines (such as trifluralin), dinitrophenols, diphenyl ethers, halogenated aliphatics, imidazolinones, inorganic herbicides, nitriles, organophosphorus herbicides, phenoxy herbicides, phenylenediamines, pyrazolyloxyacetophenones, pyrazolylphenyls, pyridazines, pyridazinones, pyridines, pyrimidinediamines, quaternary ammonium herbicides, thiocarbamates, thiocarbonates, triazines (such as atrazine), triazinones, triazoles, triazolopyrimidines, uracil herbicides, urea herbicides, unclassified herbicides, or a mixture thereof.

The agricultural compositions described herein may act as a nutrient source for microbial agents, thereby stimulating their growth. Alternatively, the application of the composition to the soil may result in an exothermic reaction which attracts the microbes, thereby bringing them to a nutrient rich environment. The term "microbial agent" is meant to include microorganisms that enhance biodegradation processes. These microorganisms include bacteria, fungi, and algae, or combinations of these microorganisms, for example. Furthermore, as used herein, "biodegradation" means the chemical alteration and breakdown of a substance caused by microorganisms and their enzymes. Contaminants that are biodegradable include any compound that can be microbially mineralized into carbon dioxide, water, ammonia and/or chloride, or that can be transformed into a non-hazardous intermediate.

As a method for enhanced bioremediation, oxidized surfactant can be applied to a contaminated area in a generally pure state; diluted with a suitable liquid solvent (aqueous or otherwise); or mixed with a suitable solid core material. The surfactant may also be diluted with a solvent prior to mixing with the solid core material. In addition the composition may further comprise any biological agent compatible with the present invention. Exemplary biological agents include pesticides, herbicides, insecticides, growth regulators, toxicants, bactericides, molluscicides, chemosterilants, rodenticides, avicides, nematicides, acaricides, algicides, fungicides, predicides, or any variant or combination thereof.

As a method for enhanced bioremediation, the amount of oxidized polyglycol ether applied to soil is preferably between about 0.6 pounds per acre and about 8.5 pounds per acre and more preferably between about 0.6 pounds per acre and about 3.5 pounds per acre.

Use of the method of the present invention further allows the soil dosage rate of a given nutrient, surfactant, or biologically active agent to be controlled over a period of time by simply selecting a fertilizer that naturally erodes more slowly or quickly. Granular fertilizer s impregnated with specific surfactants and specific biologically active agents (where used) mediate the release of the surfactant and biologically active agent with sustained and relatively predictable dosage rates. It has been found that systems can be designed in which components are released over periods ranging from days to several weeks.

The method of the present invention avoids the use of foreign materials or materials which are not otherwise useful for growing plants. It utilizes the natural slow release properties of typical granular fertilizer formulations as a vehicle for the controlled or sustained release of surfactants (with or without additional biologically active components) to soil. Thereby enhancing fertilizer nutrient uptake and efficacy of other biologically active agents. This allows for enhanced growth of plants without requiring the introduction of complex and expensive matrix components. Other controlled release fertilizer formulations do not describe the benefit of incorporating surface active agents into the matrix or formulation to improve plant nutrient utilization efficiency.

Additional methods of the present invention are directed toward the use of granular or solid fertilizers as a gradually eroding matrix from which impregnated surfactants are released to mediate their own growth promoting, herbicidal, insecticidal, chemosterilant, nematicidal, or fungicidal effects on plants over a period of time. These further methods also allow for a longer and more controlled release of the surfactant from the mixed agricultural composition. Since the controlled release more efficiently controls the release of the surfactant, the total amount required is lowered and the cost is reduced. Also, the use of complex and expensive matrix components containing foreign materials or materials which are not otherwise useful for growing plants is avoided.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1: Mixing the Fertilizer Blend

Often dry fertilizers are mixed with small amounts of additives through the use of large blending devices. In some cases, a payloader is used in which the components are blended through the process of picking large scoopfulls of a fertilizer component and spreading it over another component. Transfer of scoopfulls of components into the mixture with a spreading action eventually achieves an evenly distributed mixture. Other methods for mixing dry fertilizer are well known in the art. For example, a large drum shaped container capable of holding the desired volume of dry ingredients and able to rotate at an inclined angle along the center axis may be used. Dry components are added to the drum during rotation to facilitate a mixing or blending action. Often times the drum has a method for spraying liquid mixtures onto the dry fertilizer components. This serves to impregnate or coat the surface of the fertilizer blend with these liquid materials. Often these methods of incorporating a liquid material into a fertilizer matrix involve the use of a liquid pump and nozzles to propel small droplets onto the dry fertilizer components so that the liquid is evenly distributed.

During the process of mixing, a small amount of fluid such as a nonionic surfactant, such as TERGITOL (Union Carbide Corp., Danbury, Conn.) or NEODOL (NEODOL is a registered trademark of Shell Chemical Corp., Houston, Tex.), may be sprayed onto the mixture to achieve a uniform coating on the particles. At this time a pesticide may be incorporated into the mixture following rate guidelines specified by the pesticide label.

By using different amounts of a given fertilizer component, a desired level and ratio of nitrogen, phosphorous and potassium also known as the NPK values, may be achieved. For example to produce a U.S. ton of a mixture containing an NPK level of 16-16-18 one would mix 700 pounds of urea to 700 pounds of super triple phosphate to 600 pounds of course potash. This fertilizer blend has an NPK composition of 22-4-12+7S.

Example 2: Production of an Agricultural Composition Comprising Fertilizer Mixed with TERGITOL 15-S-9

In a large blending device the following materials were added during the mixing process: 384 pounds of Course Potash; 174 pounds of Diammonium Phosphate (DAP); 584 pounds of Ammonium Sulfate; 858 pounds of Ammonium Nitrate. These materials were blended until an even distribution was achieved. During the later stages of this blending process, the liquid surfactant TERGITOL 15-S-9 (Union Carbide Corp., Danbury, Conn.) was sprayed onto the dry mixture of fertilizer. The liquid was sprayed by the use of a pump to pressurize the liquid and nozzles to control and direct the spray. In this example, 8 quarts of the liquid TERGITOL (>97% v/v alkyloxypolyethylene-oxyethanol) were sprayed onto the blended fertilizer. As the TERGITOL reaches a high level, the mixture becomes somewhat wet and difficult to manage. As this occurs, drying agents such as bentonite clay or calcium sulfate may be used at a rate of between 5–50 pounds per U.S. ton of fertilizer mixture.

Example 3: Production of a Agricultural Composition Comprising Fertilizer Mixed with NP-9

The composition was prepared as outlined in Example 1 with the exception that 8 quarts of NP-9 (>95% alpha-4(4-nonylphenol)-omega-hydroxy-poly(oxy-1,2-ethanediyl); is Union Carbide Corp., Danbury, Conn.) were sprayed onto the dry fertilizer blend.

Example 4: Oxidation of TERGITOL 15-S-9 Using Sodium hypochlorite

In a reaction vessel 10 quarts (9.5 liters) of bleach (about 5.25% sodium hypochlorite by weight) and 10 quarts (9.5 liters) TERGITOL 15-S-9 were mixed. This was stirred well and allowed to react for about 2 hours. Oxidized products were identified by infrared spectroscopy. Infrared spectroscopy analysis showed the presence of a terminal C=O (indicated by the presence of an absorption peak centered at 1715 cm$^{-1}$, no peaks are observed in the 1800-1600 cm$^{-1}$ region for the virgin compound).

Example 5: Testing the Growth Promoting Properties of Agricultural Compositions Comprising Fertilizer mixed with Surfactants The compositions of Examples 2 and 3 were tested for promotion of plant growth by treatment of Kentucky Bluegrass turfs in individual treatment plots of 10 square feet each. A total of 45 plots were constructed with 3 replications for each treatment. The specific varieties of turfs studied included Abby, Glade, Shamrock, Wildwood and midnight grasses. The growth of the grasses was assessed by measuring the length and weight of grass clippings collected over specified periods of time.

The compositions of Examples 2 and 3 were applied to independent test plots at a rate of 125, 250 and 500 pounds/acre and compared to plots treated with only non-coated fertilizer applied at the same rates. Comparisons were also made to test plots treated with liquid surfactant alone (SAFE-T GREEN, a composition comprising a blend of TERGITOL 15-S-9 and 15-S-3 at an approximate ratio of about 90 to about 10 v/v, a product of Safe Materials Inc., Valdosta, Ga.), and plots receiving no treatment. The liquid surfactant was applied to the turf at a rate of 1 quart/acre. Results are provided in Tables 1 and 2.

TABLE 1

Average Weight (grams) of Grass Clippings Collected on Given Dates

| Treatment | 7/29/98 | 8/11/98 | 8/20/98 | 9/3/98 | 9/23/98 | 10/1/98 |
|---|---|---|---|---|---|---|
| 1 | 419.0 | 1280.8 | 556.0 | 393.7 | 556.7 | 373.8 |
| 2 | 607.5 | 1967.8 | 857.5 | 557.4 | 730.9 | 514.5 |
| 3 | 586.5 | 1795.2 | 778.5 | 527.7 | 625.7 | 393.9 |
| 4 | 552.5 | 1395.8 | 703.8 | 479.2 | 545.3 | 317.4 |
| 5 | 484.1 | 1214.5 | 564.9 | 388.3 | 449.3 | 283.6 |
| 6 | *NR | *NR | *NR | 447.2 | 711.1 | 447.5 |
| 7 | *NR | *NR | *NR | 427.3 | 667.9 | 430.2 |

Treatments:
1 TERGITOL 15-S-9/fertilizer mixture applied at a rate of 250 lb/acre
2 TERGITOL 15-S-9/fertilizer mixture applied at a rate of 500 lb/acre
3 TERGITOL 15-S-9/fertilizer mixture applied at a rate of 125 lb/acre
4 SAFE-T-GREEN applied at a rate of 1 Quart/acre
5 Control; No application
1. NP-9/fertilizer mixture applied at a rate of 250 lb/acre
2. Fertilizer blend of Example 1 at a rate of 250 lb/acre without the addition of a surfactant
*NR Not Recorded

TABLE 2

Average Length (inches) of Grass Clippings Collected on Given Dates

| Treatment | 7/29/98 | 8/11/98 | 8/20/98 | 9/3/98 | 9/23/98 | 10/1/98 |
|---|---|---|---|---|---|---|
| 1 | 2.69 | 3.11 | 2.61 | 2.11 | 2.08 | 2.25 |
| 2 | 2.52 | 3.83 | 3.28 | 2.28 | 2.22 | 2.61 |
| 3 | 2.61 | 3.58 | 3.17 | 2.31 | 2.28 | 2.08 |
| 4 | 2.67 | 3.28 | 3.00 | 2.17 | 2.06 | 1.67 |
| 5 | 2.53 | 3.03 | 2.56 | 2.06 | 1.81 | 1.67 |
| 6 | *NR | *NR | *NR | 2.17 | 2.97 | 2.58 |
| 7 | *NR | *NR | *NR | 2.22 | 2.64 | 2.67 |

Treatments:
1. TERGITOL 15-S-9/fertilizer mixture applied at a rate of 250 lb/acre
2. TERGITOL 15-S-9/fertilizer mixture applied at a rate of 500 lb/acre
3. TERGITOL 15-S-9/fertilizer mixture applied at a rate of 125 lb/acre
4. SAFE-T GREEN applied at a rate of 1 Quart/acre
5. Control; No application
6. NP-9/fertilizer mixture applied at a rate of 250 lb/acre
7. Fertilizer blend of Example 1 at a rate of 250 lb/acre without the addition of a surfactant
*NR Not Recorded As the results indicate, the surfactant/fertilizer mixtures, when applied at a rate of 250 lb/acre significantly stimulated plant growth relative to treatments with surfactant alone. In addition, the NP-9/fertilizer mixture (Treatment No. 6) outperformed the unmixed fertilizer (Treatment No. 7). While the data suggest that the TERGITOL- 15-S-9/fertilizer mixture (Treatment No. 2) did not stimulate growth as well as the unmixed fertilizer (Treatment No. 7), this result is considered to be an anomaly. The result is not consistent with observations made in several similar experiments.

Example 6: Testing the Toxicity of Surfactant/Fertilizer Mixtures on Soil Microbes The effect of soil treatment with the surfactant/fertilizer mixtures on the microbial activity in the soil was assessed. Samples of soil were collected from each of the treated plots in Example 5, above. Microbial activity was assessed by culturing the soil in agar media and determining the number of colonies that form. Mold and yeast were cultured on Acidified Potato Dextrose Agar at 21° C. for 5 days. Aerobic bacteria and microbes were cultured in Tryptic Soy Agar at 35° C. for 48 hours. Results are expressed as the number of colony forming units (CFU) per gram of collected soil. In addition to the crude counts, the colonies were also counted on the basis of the types of microbes. The results are provided in Table 3.

TABLE 3

Antimicrobial Activity of Surfactant/Fertilizer Mixtures

| Treatment | CFU Type | Pre-treatment | 40 Days | 55 days | 70 Days |
|---|---|---|---|---|---|
| 1 | Mold | 23,000 | 95,850 | 575,000 | 1,365,000 |
|   | Plate Count | 3,000,000 | 8,950,000 | 26,070,000 | 10,825,000 |
| 2 | Mold | 54,000 | 1,872,000 | 447,500 | 157,500 |
|   | Plate Count | 3,750,000 | 23,000,000 | 16,050,000 | 9,300,000 |
| 3 | Mold | 150,000 | 29,025 | 316,000 | 245,000 |
|   | Plate Count | 2,900,000 | 4,900,000 | 9,620,000 | 5,260,000 |
| 4 | Mold | 100,000 | 165,500 | 98,250 | 380,000 |
|   | Plate Count | 3,400,000 | 2,800,000 | 13,770,000 | 4,550,000 |
| 5 | Mold | 26,000 | 31,500 | 350,000 | 175,000 |
|   | Plate Count | 1,150,000 | 5,600,000 | 14,770,000 | 3,505,000 |
| 6 | Mold | *NR | *NR | 145,250 | 497,500 |
|   | Plate Count | *NR | *NR | 15,170,000 | 25,050,000 |

Treatments:
1. TERGITOL 15-S-9/fertilizer mixture applied at a rate of 250 lb/acre
2. TERGITOL 15-S-9/fertilizer mixture applied at a rate of 500 lb/acre
3. TERGITOL 15-S-9/fertilizer mixture applied at a rate of 125 lb/acre
4. SAFE-T GREEN applied at a rate of 1 Quart/acre
5. Control: No treatment
6. NP-9/fertilizer mixture applied at a rate of 250 lb/acre
*NR Not Recorded As the results indicate, the surfactant/fertilizer mixtures displayed reduced toxicity relative to the surfactant treatment alone. Treatments 1 and 6 allowed for higher amounts of microbial growth over a longer period of time than the surfactant treatment alone. The surfactant significantly reduced the microbial growth in the soil relative to the mixed fertilizer treatments. This suggests that the surfactant/fertilizer mixtures allow a more uniform release of its components into the soil.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods in the steps or in the sequence of steps of the methods described herein without departing from the concept, spirit and scope of the invention. It will also be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. An agricultural composition prepared by a process comprising mixing together a polyglycol ether and an oxidizing agent selected from the group consisting of naphdaleneacetic acid, chromic acid, permanganate and hypochlorite together with a soil additive carrier, said carrier comprising a fertilizer, anti-caking agent, pesticide, or combination thereof, and said polyglycol ether comprising less than about 1.0 % of the composition.

2. The agricultural composition of claim 1, wherein the carrier is an aqueous or non-aqueous liquid solvent.

3. The agricultural composition of claim 1, wherein, the carrier is a solid core material comprising a powdered, particulate, granular, or pelleted form.

4. The agricultural composition of claim 1, wherein the fertilizer is ammonium nitrate, ammonium sulfate, ammonium polyphosphate, calcium nitrate, calcium sulfate, diammonium phosphate, triple super phosphate, single super phosphate, lime or limestone, magnesium sulfate, manganese sulfate, monoammonium phosphate, monocalcium phosphate, potassium nitrate, potassium chloride, potassium magnesium sulfate, sulfate of potash, sodium nitrate, sulfurcoated urea, borax, pelleted fertilizers, fertilizers coated for slow release, or mixtures thereof.

5. The agricultural composition of claim 3, wherein the soil additive is diatomaceous earth, calcium sulfate, corn cob particulate, bentonite clay, vermiculite, or combinations of these substances.

6. The agricultural composition of claim 1, wherein the polyglycol ether is an alcohol ethoxylate, fatty alcohol ethoxylate, or alkylphenol ethoxylate.

7. The agricultural composition of claim 1, wherein the polyglycol ether is represented by the formula:

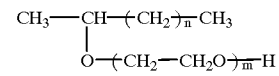

wherein m and n are integers, n is from 9 to 15, and m is from 3 to 40.

8. The agricultural composition of claim 7, wherein the polyglycol ether is represented by the formula:

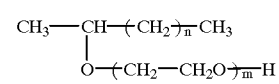

wherein m and n are integers, n is from about 9 to about 11, and m is about 15.

9. The agricultural composition of claim 3, wherein between about 400 grams and about 7700 grams of the oxidized polyglycol ether are mixed with each U.S. ton of solid core material.

10. The agricultural composition of claim 3, wherein between about 400 grams and about 2900 grams of the oxidized polyglycol ether are mixed with each U.S. ton of solid core material.

11. The agricultural composition of claim 1, wherein the polyglycol ether is represented by the formula:

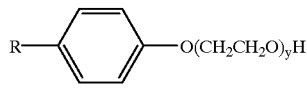

wherein R is a straight or branched carbon chain containing from about 1 to about 30 carbon atoms and y is an integer between about 5 and about 15.

12. The agricultural composition of claim 11, wherein the polyglycol ether is represented by the formula:

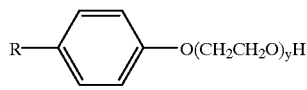

wherein R is a straight or branched carbon chain containing about 9 carbon atoms and y is an integer between about 9 and about 10.

13. The agricultural composition of claim 3, further comprising a drying agent.

14. The agricultural composition of claim 13, wherein the drying agent is calcium sulfate or bentonite clay.

15. The agricultural composition of claim 1, further comprising an insecticide, an herbicide, a nematicide, a fungicide, or a chemosterilant or mixtures thereof.

16. A method of promoting the growth of plants in soil comprising:
   mixing together an oxidation product of a polyglycol ether with a carrier; and
   applying the agricultural composition to soil.

17. The method of claim 16, wherein the carrier is an aqueous or non-aqueous liquid solvent.

18. The method of claim 16, wherein the carrier is a solid core material comprising a powdered, particulate, granular, pelleted, or solid form of a fertilizer.

19. The method of claim 16, wherein the polyglycol ether is an alcohol ethoxylate, fatty alcohol ethoxylate, or alkylphenol ethoxylate.

20. An agricultural composition prepared by a process comprising mixing together oxidation products of a polyglycol ether with a solid core soil additive wherein the soil additive is a fertilizer, anti-caking agent, pesticide, or combination thereof, and said polyglycol ether comprising less than about 1.0 % of the composition.

21. The agricultural composition of claim 20, wherein the soil additive is a powdered, particulate, granular, or pelleted form.

22. The agricultural composition of claim 20, wherein the fertilizer is ammonium nitrate, ammonium sulfate, ammonium polyphosphate, calcium nitrate, calcium sulfate, diammonium phosphate, triple super phosphate, single super phosphate, line or limestone, magnesium sulfate, manganese sulfate, monoammonium phosphate, monocalcium phosphate, potassium nitrate, potassium chloride, potassium magnesium sulfate, sulfate of potash, sodium nitrate, sulfur-coated urea, borax, pelleted fertilizers, fertilizers coated for slow release, or mixtures thereof.

23. The agricultural composition of claim 20, wherein the soil additive is diatomaceous earth, calcium sulfate, corn cob particulate, bentonite clay, vermiculite, or combinations of these substances.

24. The agricultural composition of claim 20, wherein between about 400 grams and about 7700 grams of the oxidized polyglycol ether are mixed with each U.S. ton of solid core material.

25. The agricultural composition of claim 20, wherein between about 400 grams and about 2900 grams of the oxidized polyglycol ether are mixed with each U.S. ton of solid core material.

26. An agricultural composition prepared by a process comprising mixing together oxidation products of a polyglycol ether with a carrier, wherein the polyglycol ether is represented by the formula:

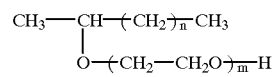

wherein m and n are integers, n is from 9 to 15, and m is from 3 to 40 and said polgycol ether comprises less than about 1.0 % of the composition.

27. The agricultural composition of claim 26, wherein the polyglycol ether is represented by the formula:

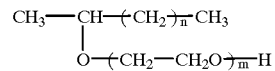

wherein m and n are integers, n is from about 9 to about 11, and m is about 15.

28. An agricultural composition prepared by a process comprising mixing together oxidation products of a polyglycol ether with a career, wherein the polyglycol ether is represented by the formula:

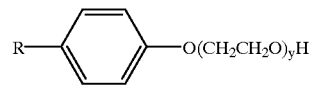

wherein R is a straight or branched carbon chain containing from about 1 to about 30 carbon atoms and y is an integer between about 5 and about 15 and said polyglycol ether comprises less than about 1.0 % of the composition.

29. The agricultural composition of claim 28, wherein the polyglycol ether is represented by the formula:

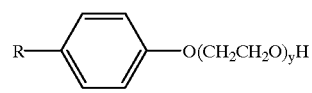

wherein R is a straight or branched carbon chain containing about 9 carbon atoms and y is an integer between about 9 and about 10.

* * * * *

UNITED STATES PATENT AND TRADEMARK OFFICE
CERTIFICATE OF CORRECTION

PATENT NO.    : 6,110,866
DATED         : August 29, 2000
INVENTOR(S)   : Walker It is certified that error appears in the above-identified patent and that said Letters Patent is hereby corrected as shown below:

Column 12,
Lines 10-11, delete "naphdaleneacetic" and replace with -- naphthaleneacetic --.
Line 18, "wherein, the" and replace with -- wherein the --.

Column 14,
Line 35, delete "career" and replace with -- carrier --.

Signed and Sealed this

Fourteenth Day of August, 2001

*Attest:*

*Attesting Officer*

NICHOLAS P. GODICI
*Acting Director of the United States Patent and Trademark Office*